United States Patent [19]

Bice et al.

[11] 4,425,790
[45] Jan. 17, 1984

[54] PREDICTION OF EXTRUSION PERFORMANCE OF POLYMERS

[75] Inventors: William L. Bice, Slaughter; Ernest D. Graves, Jr.; Gerald P. Wagener, both of Baton Rouge, all of La.

[73] Assignee: The Dow Chemical Company, Midland, Mich.

[21] Appl. No.: 332,681

[22] Filed: Dec. 21, 1981

[51] Int. Cl.³ .......................................... G01N 11/08
[52] U.S. Cl. ..................................................... 73/55
[58] Field of Search .................................... 73/55, 56

[56] References Cited

U.S. PATENT DOCUMENTS

| | | | |
|---|---|---|---|
| 3,138,950 | 6/1964 | Welty et al. | 73/55 |
| 3,203,225 | 8/1965 | Sieglaff et al. | |
| 3,209,581 | 10/1965 | Crane et al. | 73/55 |
| 3,252,320 | 5/1966 | Welty | 73/56 |
| 3,302,451 | 2/1967 | Martin | 73/55 |
| 3,375,704 | 4/1968 | Thompson, Jr. et al. | 73/55 |
| 3,468,158 | 9/1969 | Chien | 73/55 |
| 3,559,464 | 2/1971 | Foust et al. | 73/55 |
| 3,595,305 | 7/1971 | Welty et al. | 165/47 |
| 3,610,026 | 10/1971 | Topham | 73/55 |
| 3,841,147 | 10/1974 | Coil et al. | 73/56 |
| 4,157,029 | 6/1979 | Leca et al. | 73/55 |

Primary Examiner—S. Clement Swisher
Assistant Examiner—Joseph W. Roskos
Attorney, Agent, or Firm—A. J. Young

[57] ABSTRACT

An apparatus is provided for predicting the extrusion performance of a thermoplastic resinous polymer, which includes at least three and preferably four capillaries arranged in series with each successive capillary having a larger passageway than that of the immediately preceding capillary and with each capillary having substantially the same ratio of passageway length to cross-sectional area. The apparatus also includes a pump for forcing a heated polymer melt through the capillaries at a constant volumetric flow rate, a sensor for measuring the temperature of the polymer melt, a sensor for measuring the pressure drop of the polymer across each capillary, and a combination recorder and processor for determining the polymer viscosity in each capillary (different shear rates), whereby the extrusion performance of the polymer can be predicted. A method for predicting extrusion performance of a thermoplastic resinous utilizing these polymer capillaries is also provided.

8 Claims, 1 Drawing Figure

PREDICTION OF EXTRUSION PERFORMANCE OF POLYMERS

BACKGROUND OF THE INVENTION

This invention relates to the rheological characterization of thermoplastic resinous polymers. More particularly, the invention relates to the continuous and simultaneous measurement of polymer viscosity over a wide range of shear rates, whereby the extrusion performance of a polymer can be predicted.

For predicting polymer processability, rheological characterization over a wide range of shear rates is necessary. This characterization generally takes the form of a flow curve, which is a logarithmic plot of shear stress or viscosity against shear rate. Such commonly used tests as melt index (ASTM D-1238) are inadequate for this purpose, since they define only one point on the flow curve, and that point is in a shear-rate range well below normal processing shear rates. Even a two-point measurement is not adequate, since flow curves for non-Newtonian fluids exhibit significant changes in slope over any appreciable range of shear rates.

SUMMARY

In general, this invention provides an apparatus and a method for predicting the extrusion performance of a thermoplastic resinous polymer. The apparatus includes first, second, and third capillaries in series having substantially the same ratio of passageway length to cross-sectional area, each successive capillary having a larger passageway than that of the immediately preceding capillary; means for forcing the polymer to flow through the first, second, and third capillaries in series at a substantially constant volumetric rate; and means for sensing the pressure drop across the first, second, and third capillaries.

For a given polymeric material, the shape and location of the curve are greatly influenced by the geometry of the passageways for the capillaries used to make the measurements. While the passageway cross-section of the capillaries is normally circular, the cross-section may be defined by other shapes such as a square or a rectangle. Flow-curve data obtained with capillaries having different passageway sizes would not generally correlate or be compatible. However, in the present invention, compatibility is achieved by keeping the ratio of passageway length to cross-sectional area of all the capillaries substantially the same.

The method of the present invention includes the steps of (a) providing an apparatus with first, second, and third capillaries in series having substantially the same ratio of passageway length to cross-sectional area, each successive capillary having a larger passageway than that of the immediately preceding capillary; (b) forcing a thermoplastic resinous polymer to flow through the first, second, and third capillaries in series at a substantially constant volumetric rate; (c) measuring first, second, and third pressure drops across the first, second, and third capillaries, respectively; and (d) converting the volumetric rate and pressure drops to a graphic plot of polymer viscosity at different shear rates.

The present invention is directed to the determination of polymer viscosity at as many different shear rates as necessary for a reasonably accurate definition of any of the commonly used flow-curve equations. This determination is accomplished by measuring the pressure drop across each capillary of at least three and preferably four capillaries in series, at a constant volumetric flow rates. The apparent viscosity $N_a$ is calculated from the equation $$N_a = T_a/G_a \quad (1)$$

Apparent shear stress $T_a$ and apparent shear rate $G_a$ through a capillary are, respectively, $$T_a = PD/4L \quad (2)$$

and $$G_a = 32Q/\pi D^3 \quad (3)$$

where P is the pressure drop, Q is the volumetric flow rate, L is the capillary passageway length, and D is the internal diameter of the capillary passageway.

The above equation (3) for apparent shear rate is strictly applicable only to Newtonian fluids. For non-Newtonian fluids such as most polymer melts, true shear rate G can be determined by the Rabinowitsch correction, $$G = G_a(3S+1)/4S \quad (4)$$

where S is the slope, which is defined as the derivative of the logarithm of $T_a$ to the base ten with respect to the logarithm to the base ten of $G_a$; $d \log_{10} T_a/d \log_{10} G_a$.

Similarly, if true shear stress is desired, the above equation (2) for apparent shear stress must be modified. The pressure term therein should represent the pressure drop along the length L of the capillary passageway, but the only measurable pressure drop includes an "end effect"; viz., pressure drop at the capillary inlet. Conventionally, this correction is made through a technique developed by Bagley from the equation $$T = PD/(4L - E) \quad (5)$$

where E is an end correction determined by taking data at identical shear rates with a series of capillaries having different length-to-diameter (L/D) ratios of passageways.

When the present invention is practiced with cylindrical passageways, all capillaries having a ratio of passageway length to diameter that is greater than about twenty to one. This is sufficient to make the pressure drop at the capillary inlet negligible compared with the total pressure drop across the capillary, thereby making $T_a$ substantially equal to T. Beneficially, the value of this ratio should lie between about ten to one and about one hundred to one, and preferably between about forty to one and about sixty to one.

In addition to its utility for predicting polymer processability, a flow curve, through mathematical analysis, allows calculation of such fundamental rheological parameters as zero-shear viscosity and characteristic relaxation time. These parameters, in turn, allow estimation of such useful parameters as average molecular weight and molecular-weight distribution.

Examples of problems soluble by the method of the present invention include:

(1) Calculation of the constants $A_o$, $A_1$, and $A_2$ in the empirical flow-curve equation $$\log T_a = A_o + A_1 \log G_a + A_2 (\log G_a)^2 \quad (6)$$

(2) Determination of the Rabinowitsch correction factor at any shear rate, using equation (6) and the equation for the true viscosity, N, $$N = A_1 + A_2 \log G_a \quad (7)$$

(3) Determination of zero-shear viscosity $N_o$, limiting viscosity $N_h$ at very high shear rates, and characteristic time constant K in the Cross equation $$N = N_h + (N_o - N_h)/(1 + KG^{2/3}) \quad (8)$$

(4) Estimation of weight-average molecular weight $M_w$ from the relationship $$M_w = CN_o^B \quad (9)$$

(5) Estimation of number-average molecular weight $M_n$ from the relationship $$M_n = aN_n^b \quad (10)$$

where a and b are constants; and (6) Estimation of swell properties from the time constant K.

While the method of the present invention applies generally to non-Newtonian fluids such as polymer melts, polyethylene is especially suitable as a polymer whose extrusion performance is predictable by means of the invention.

It is an object of this invention to provide the technology for predicting the extrusion performance of a thermoplastic resinous polymer. It is a further object of the invention to provide the technology for rheologically characterizing a polymer. It is a still further object of the invention to provide the technology for defining a flow curve for a polymer. Other objects of the invention will be apparent to those skilled in the art from the more detailed description which follows.

DESCRIPTION OF THE PREFERRED EMBODIMENT

Figure 1:
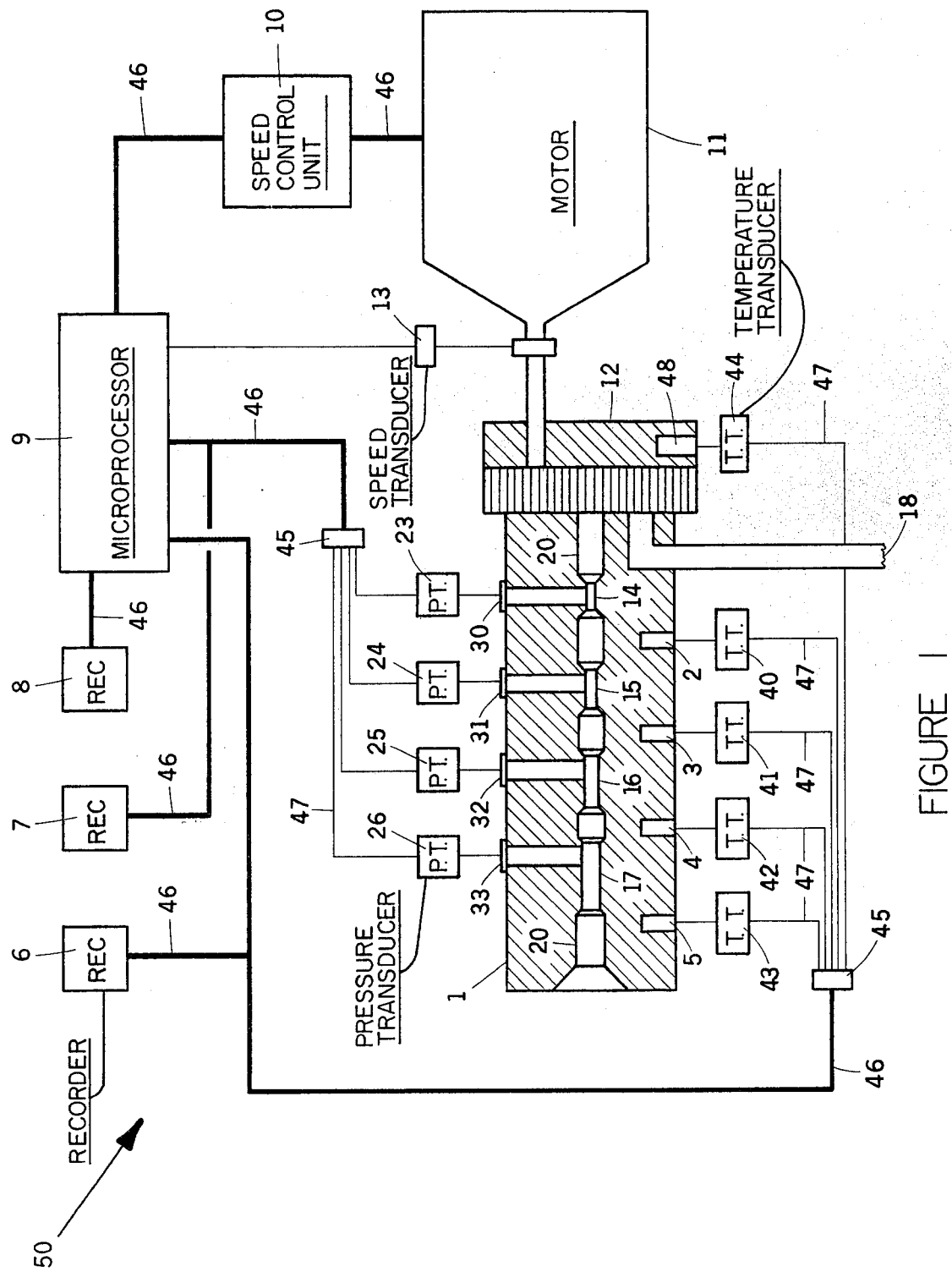
FIG. 1 is a schematic representation of an apparatus made in accordance with the present invention.

The following description illustrates the manner in which the principles of this invention are applied, but is not to be construed as in any sense limiting the scope of the invention.

More specifically, referring to FIG. 1, molten polymer from an extruder (not shown) is introduced into the apparatus 50 at the inlet 18 of a precision-metering pump 12 driven by an electrical direct-current motor 11 coupled to a gear-reduction unit (not shown) and a speed-control unit 10. The pump 12 provides the means for forcing the polymer to flow through the apparatus 50 at a substantially constant volumetric rate, and for providing different flow rates of the polymer.

The polymer flows through a channel 20 in a die assembly 1 which is ample in size to effect temperature equilibration of the polymer. The die assembly 1 is heated by split-band heaters (not shown) which provide the means for controlling the temperature of the polymer. After temperature equilibration, the polymer flows through the cylindrical passageways of first, second, third, and fourth capillaries 14, 15, 16, and 17, respectively.

The first, second, third, and fourth capillaries 14, 15, 16, and 17, respectively, have substantially the same ratio of passageway length to diameter. In addition, the capillaries 14, 15, 16, 17 are so sized that each successive capillary has a larger passageway than that of the preceding capillary. Thus, for a constant volumetric flow rate of the polymer, the shear rate decreases as the polymer flows through the series of capillaries 14, 15, 16, 17. Pressure measurements are obtained from first, second, third, and fourth pressure sensors 30, 31, 32, and 33, respectively, disposed in the passageways near the inlets of the first, second, third, and fourth capillaries 14, 15, 16, and 17, respectively. The polymer melt leaves the outlet of the fourth capillary 17 at substantially atmospheric pressure, thereby eliminating the need for a fifth pressure sensor. From the four pressure measurements associated with the four capillaries 14, 15, 16, 17, the pressure drop across each capillary is readily calculated.

The pressures sensed by the first, second, third, and fourth pressure sensors 30, 31, 32, and 33, respectively, are converted by first, second, third, and fourth pressure transducers 23, 24, 25, and 26, respectively, into electrical signals which are input to a first recorder 7 and to a microprocessor 9. The flow rate of the polymer is determined by the speed of the pump 12. A speed transducer 13 converts pump speed into an electrical signal, thereby providing the means for sensing the flow rate of the polymer. The electrical signal generated by the speed transducer 13 is input to the microprocessor 9 through an electrical lead 49. Polymer temperature is sensed by first, second, third, fourth, and fifth platinum-resistance temperature sensors 2, 3, 4, 5, and 48, respectively, converted into electrical signals by first, second, third, fourth, and fifth temperature transducers 40, 41, 42, 43, and 44, respectively, and input to a second recorder 6 and to the microprocessor 9.

Electrical leads 47 from the pressure transducers 23, 24, 25, 26, and from the temperature transducers 40, 41, 42, 43, 44 are beneficially conveyed through shielded cables 46 to the first and second recorders 7 and 6, respectively, and to the microprocessor 9. For this purpose cable collectors 45 are provided for the leads 23, 24, 25, 26, 40, 41, 42, 43, 44.

From the four signals corresponding to the inlet pressures at the four capillaries 14, 15, 16, 17 and the signal corresponding to the speed of the pump 12, a flow curve will be defined with sufficient accuracy to calculate rheological parameters useful in predicting extrusion performance. For this purpose the microprocesso 9 is beneficially programmed to calculate these parameters and to transmit the calculated values to a third recorder 8.

While certain representative embodiments and details have been shown for the purpose of illustrating this invention, it will be apparent to those skilled in the art that various changes and modifications can be made therein without departing from the spirit and scope of the invention.

What is claimed is:

1. An apparatus for predicting the extrusion performance of a thermoplastic resinous polymer, comprising: first, second, and third capillaries in series having substantially the same ratio of passageway length to cross-sectional area, each successive capillary having a larger passageway than that of the immediately preceding capillary; means for forcing the polymer to flow through the capillaries in series at a substantially constant volumetric rate; and means for sensing the pressure drop across the first, second, and third capillaries.

2. The apparatus of claim 1, wherein the apparatus includes a fourth capillary in series with the first, second, and third capillaries, the fourth capillary having a passageway larger than that of the third capillary and a ratio of passageway length to cross-sectional area substantially equal to that of the first, second, and third capillaries.

3. The apparatus of claim 2, wherein the passageway is cylindrical and has a ratio of length to diameter of between about ten to one and about one hundred to one.

4. The apparatus of claim 3, wherein the ratio is between about forty to one and about sixty to one.

5. The apparatus of claim 4, wherein the apparatus includes means for sensing and controlling the temperature and flow rate of the polymer, and means for converting the pressures and flow rate sensed into a graphic plot of polymer viscosity at different shear rates.

6. A method for predicting the extrusion performance of a thermoplastic resinous polymer, comprising the steps of:
   (a) providing an apparatus with first, second, and third capillaries in series, each successive capillary having a larger passageway than that of the immediately preceding capillary and substantially the same ratio of capillary passageway length to cross-sectional area;
   (b) forcing the polymer to flow through the first, second, and third capillaries in series at a substantially constant volumetric rate;
   (c) measuring first, second, and third pressure drops across the first, second, and third capillaries, respectively; and
   (d) converting the volumetric rate and pressure drops to a graphic plot of polymer viscosity at different shear rates.

7. The method of claim 6 wherein the apparatus includes a fourth capillary in series with the first, second, and third capillaries, the fourth capillary having a passageway larger than that of the third capillary and a ratio of passageway length to cross-sectional area substantially equal to that of the first, second, and third capillaries, and wherein the pressure drop across the fourth capillary is measured.

8. The method of claim 7, further comprising after step (b), the step of:
   (b') sensing and controlling the temperature and flow rate of the polymer.

* * * * *